(12) United States Patent
Kennedy

(10) Patent No.: US 6,225,358 B1
(45) Date of Patent: May 1, 2001

(54) SYSTEM AND METHOD FOR CONVERTING LIGHT HYDROCARBONS TO HEAVIER HYDROCARBONS WITH IMPROVED WATER DISPOSAL

(75) Inventor: Paul Edwin Kennedy, Tulsa, OK (US)

(73) Assignee: Syntroleum Corporation, Tulsa, OK (US)

( * ) Notice: Subject to any disclaimer, the term of this patent is extended or adjusted under 35 U.S.C. 154(b) by 0 days.

(21) Appl. No.: 09/502,987

(22) Filed: Feb. 11, 2000

Related U.S. Application Data
(60) Provisional application No. 60/120,422, filed on Feb. 16, 1999.

(51) Int. Cl.$^7$ .................................................. C07C 27/00
(52) U.S. Cl. ...................... 518/700; 518/702; 518/703; 518/704; 518/708; 518/722
(58) Field of Search ........................... 518/702, 703, 518/704, 708, 700, 722

(56) References Cited

U.S. PATENT DOCUMENTS

| | | |
|---|---|---|
| 2,552,308 | 5/1951 | Buchmann et al. . |
| 2,686,195 | 8/1954 | McAdams et al. . |
| 4,973,453 | 11/1990 | Agee ..................................... 422/190 |
| 5,053,581 | 10/1991 | Hildinger et al. ................... 585/638 |
| 5,929,126 | * 7/1999 | Koveal et al. ....................... 518/709 |

\* cited by examiner

*Primary Examiner*—Johann Richter
*Assistant Examiner*—J. Parson
(74) *Attorney, Agent, or Firm*—Robert H. Johnston

(57) ABSTRACT

A system for converting lighter hydrocarbons to heavier hydrocarbons has a synthesis gas subsystem for receiving air and light hydrocarbons and producing a synthesis gas; a synthesis subsystem for receiving synthesis gas from the synthesis gas subsystem and producing heavier hydrocarbons therefrom and an aqueous byproduct stream having contaminates; and a stripper subsystem for receiving the aqueous byproduct stream and removing contaminates therefrom, wherein the stripper subsystem includes a concentrator column for concentrating contaminates in an aqueous by product stream, and a stripper column for stripping contaminates from a concentrated aqueous byproduct stream. A method for producing heavier hydrocarbons from lighter hydrocarbons includes the steps of: reacting air and a light hydrocarbon feedstock to produce a synthesis gas; delivering the synthesis gas to a Fischer-Tropsch reactor; using a Fischer-Tropsch reaction in the Fischer-Tropsch reactor to convert the synthesis gas into heavier hydrocarbons; removing contaminates from an aqueous byproduct stream; and wherein the step of removing contaminates from the aqueous byproduct stream includes the steps of: concentrating the contaminates in a concentrator column, and using the light hydrocarbons in a stripper column remove the contaminates from the byproduct stream.

8 Claims, 4 Drawing Sheets

SYSTEM AND METHOD FOR CONVERTING LIGHT HYDROCARBONS TO HEAVIER HYDROCARBONS WITH IMPROVED WATER DISPOSAL

RELATED PATENT APPLICATION.

This application claims priority of U.S. Provisional Application No. 60/120,422, filed Feb. 16, 1999.

TECHNICAL FIELD OF THE INVENTION

The present invention relates to a system and method for converting light hydrocarbons into heavier hydrocarbons and more particularly to a system and method for converting light hydrocarbons into heavier hydrocarbons with improved water disposal.

BACKGROUND OF THE INVENTION

As concerns over depletion of traditional sources of energy and over pollution rise, modern society continues to seek new sources of clean energy. One helpful approach is to convert natural gas to a synthesis gas and then synthesize longer-chain hydrocarbons with a Fischer-Tropsch reaction. To make this effective, however, it needs to be sufficiently economical.

A. Introduction To The Fischer Tropsh Process

The synthetic production of hydrocarbons by the catalytic reaction of carbon monoxide and hydrogen is well known and is generally referred to as the Fischer-Tropsch reaction. The Fischer-Tropsch reaction for converting synthesis gas (primarily CO and $H_2$) has been characterized by the following general reaction:

$$2H_2 + CO \xrightarrow{catalyst} CH_2 - + H_2O$$

The hydrocarbon products derived from the Fischer-Tropsch reaction range from some methane to high molecular weight paraffinic waxes containing more than 50 carbon atoms.

Numerous catalysts have been used in carrying out the Fischer-Tropsch reaction, and both saturated and unsaturated hydrocarbons can be produced. The synthesis reaction is very exothermic and temperature sensitive whereby temperature control is required to maintain a desired hydrocarbon product selectivity.

The Fischer-Tropsch process was developed in early part of the $20^{th}$ century in Germany. It has been practiced commercially in Germany during World War II and later in South Africa. An ongoing quest has existed, however, to improve the economics of the process.

B. Synthesis Gas Production

Synthesis gas may be made from natural gas, gasified coal, and other sources. Three basic methods have been employed for producing the synthesis gas ("syngas"), which is substantially carbon monoxide and molecular hydrogen, utilized as feedstock in the Fischer-Tropsch reaction. The two traditional methods are steam reforming, wherein one or more light hydrocarbons such as methane are reacted with steam over a catalyst to form carbon monoxide and hydrogen, and partial oxidation, wherein one or more light hydrocarbons are combusted sub-stoichiometrically to produce synthesis gas. The steam reforming reaction is endothermic and a catalyst containing nickel is often utilized. Partial oxidation is the non-catalytic, sub-stoichiometric combustion of light hydrocarbons such as methane to produce the synthesis gas. The partial oxidation reaction is typically carried out using high purity oxygen. High purity oxygen, however, can be quite expensive.

In some situations these synthesis gas production methods may be combined to form the third method. A combination of partial oxidation and steam reforming, known as autothermal reforming, has also been used for producing synthesis gas heretofore. For example, U.S. Pat. Nos. 2,552,308 and 2,686,195 disclose low-pressure hydrocarbon synthesis processes wherein autothermal reforming with air is utilized to produce synthesis gas for the Fischer-Tropsch reaction. Autothermal reforming is a combination of partial oxidation and steam reforming where the exothermic heat of the partial oxidation supplies the necessary heat for the endothermic steam reforming reaction. The autothermal reforming process can be carried out in a relatively inexpensive refractory lined carbon steel vessel whereby a relatively lower cost is typically involved.

The autothermal process results in lower hydrogen to carbon monoxide ratio in the synthesis gas than does steam reforming alone. That is, the steam reforming reaction with methane results in a hydrogen to CO ratio of about 3:1 or higher while the partial oxidation of methane results in a ratio of less than about 2:1. A good ratio for the hydrocarbon synthesis reaction carried out at low or medium pressure over a cobalt catalyst is about 2:1. When the feed to the autothermal reforming process is a mixture of light shorter-chain hydrocarbons such as a natural gas stream, some form of additional control is required to maintain the ratio of hydrogen to carbon monoxide in the synthesis gas at the optimum ratio of about 2:1. For this reason steam and/or $CO_2$ may be added to the synthesis gas reactor. See for example U.S. Pat. Nos. 4,883,170 and 4,973,453, which are assigned to the owner of this application and which are incorporated by reference herein for all purposes.

C. Introduction to Conversion Techniques and by Product Water

Numerous types of systems and reactors have been used for carrying out the Fischer-Tropsch reaction. The commercial development of the Fischer-Tropsch reactor system has included conventional fixed bed and three-phase slurry bubble column designs. Due to the complicated interplay between heat and mass transfer and the relatively high cost of Fischer-Tropsch catalysts, however, no single reactor design has dominated the commercial developments.

Many synthesis plants produce large quantities of waste water such as process condensate containing small amounts of contaminates. For example, a Fischer-Tropsch synthesis plant may produce waste water containing small amounts of alcohol and other oxygenates. A water treatment facility typically has been necessary. Such a facility might use biological treatments, which are fairly capital intensive. An approach using a stripper has been suggested in U.S. Pat. No. 5,053,581, entitled "Process For Recylcing And Purifying Condensate From A Hydrocarbon or Alcohol Synthesis Process," but has not recognized nor addressed the relative vapor to liquid (V/L) ratio required to efficiently strip the stream in order to produce high purity water.

SUMMARY OF THE INVENTION

In accordance with teachings of the present invention, a conversion system and method are provided that address shortcomings and problems with previous systems and methods. According to one aspect of the present invention, a system for converting lighter hydrocarbons to longer-chain hydrocarbons includes a synthesis gas subsystem for receiving an oxygen-containing gas, such as air, and light hydrocarbons and producing a synthesis gas; a synthesis subsystem for receiving synthesis gas from the synthesis gas subsystem and producing longer-chain hydrocarbons therefrom and an aqueous byproduct stream having contaminates; and a stripper subsystem for receiving the aqueous byproduct stream and removing contaminates therefrom, wherein the stripper subsystem includes a concentrator column for concentrating contaminates in an aqueous by product stream, and a stripper column for receiving light hydrocarbons to strip contaminates from a concentrated aqueous byproduct stream.

According to another aspect of the present invention, a method for producing heavier hydrocarbons from lighter hydrocarbons includes the steps of: reacting air (or other oxygen-containing gas) and a light hydrocarbon feedstock to produce a synthesis gas; delivering the synthesis gas to a Fischer-Tropsch reactor; using a Fischer-Tropsch reaction in the Fischer-Tropsch reactor to convert the synthesis gas into heavier hydrocarbons; removing contaminates from an aqueous byproduct stream; and wherein the step of removing contaminates from the aqueous byproduct stream comprises the steps of: concentrating the contaminates in a concentrator column, and using the light hydrocarbons in a stripper column to remove the contaminates from the byproduct stream.

Technical advantages of the present invention include that it provides a system and method for cleaning up water for disposal at relatively reduced cost from previously known systems and techniques. Another technical advantage of the invention is that it allows for an increase in the carbon content of the light hydrocarbon feedstock.

BRIEF DESCRIPTION OF THE DRAWINGS

For a more complete understanding of the present invention and its advantages, reference is now made to the following description taken in conjunction with the accompanying drawings in which.

DETAILED DESCRIPTION OF THE INVENTION

The preferred embodiments of the present invention and its advantages are best understood by referring to FIGS. 1–5 of the drawings, like numerals being used for like and corresponding parts of the various drawings.

Figure 1:
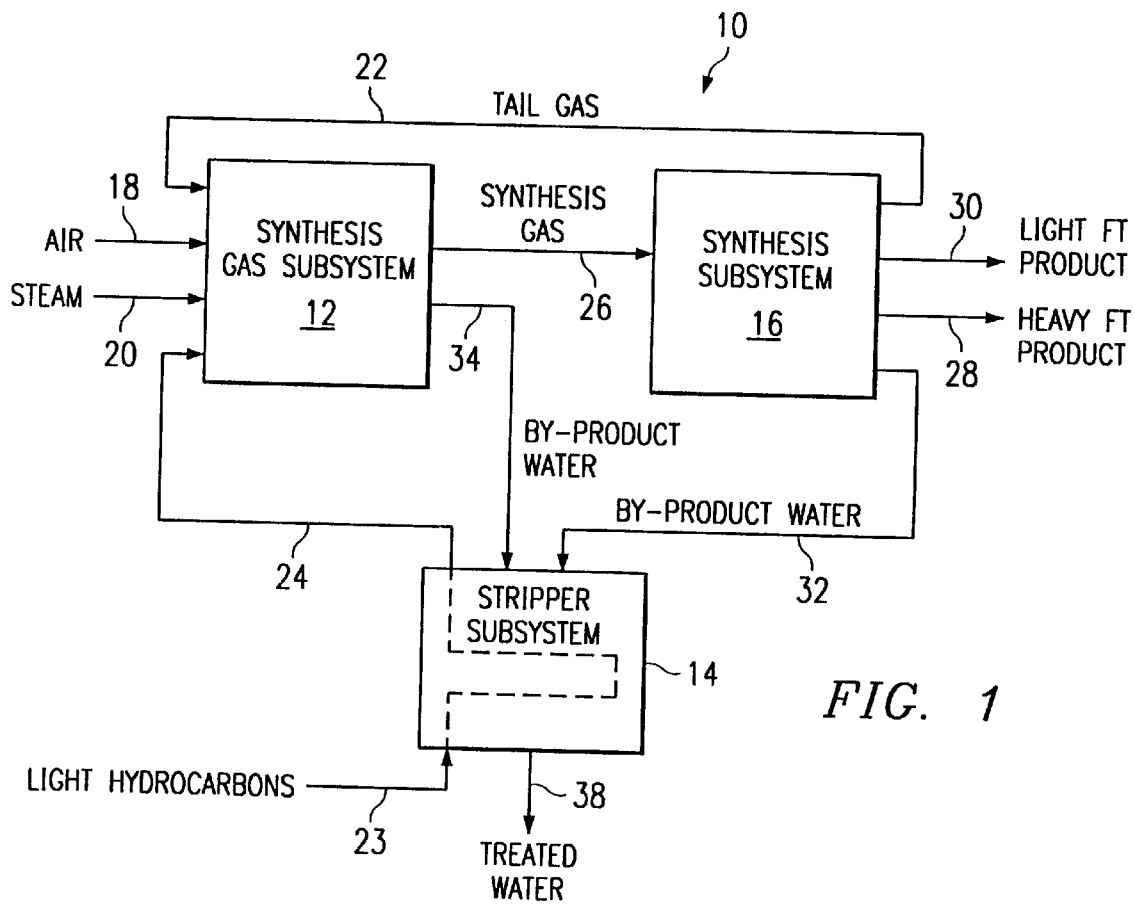
FIG. 1 is a schematic diagram of a system according to one embodiment of the present invention.

Referring now to FIG. 1, a system 10 for converting lighter, shorter-chain hydrocarbons to heavier, longer-chain hydrocarbons with an improved water disposal system is presented. A synthesis gas subsystem 12 receives a plurality of feedstocks and produces synthesis gas, which includes primarily hydrogen and carbon monoxide. The synthesis gas is delivered to a synthesis subsystem 16 where heavier, longer-chain hydrocarbons are formed. As will be described further below, one or more of the plurality of feedstocks may be enriched with respect to carbon through a stripper (or contaminant removal) subsystem 14. The stripper subsystem 14 strips or helps to remove contaminants from one or more byproduct water streams delivered to it from the synthesis gas subsystem 12 and/or the synthesis subsystem 16.

The plurality of feed streams to the synthesis gas subsystem 12 may include an oxygen-containing gas such as air or enriched air, which is shown delivered through conduit 18; steam, which is shown delivered through conduit 20; a low-BTU residue, or tail gas, which is delivered through conduit 22; and light hydrocarbons, which are shown delivered through conduit 24. The hydrocarbon feedstock delivered through conduit 24 is a hydrocarbon feedstock that has been carbon enriched by stripper subsystem 14. The synthesis gas prepared by synthesis gas subsystem 12 is delivered through synthesis gas conduit 26 to synthesis subsystem 16.

Synthesis gas subsystem 12 may utilize a partial oxidation system, a steam reformer, or preferably an autothermal reformer. While conduit 18 is shown delivering air, it is to be understood that in some applications it may be desirable to use enriched air or other oxygen-containing gases, and the term "air" should be considered to include enriched air as well. By "enriched air," an air with an oxygen content above standard air is meant, i.e., above about 21 percent oxygen.

Synthesis subsystem 16 receives synthesis gas from subsystem 12 and uses a reactor or reactors to produce heavier, longer-chain hydrocarbons preferably using the Fischer-Tropsch reaction. The synthesis subsystem 16 produces a heavy Fischer-Tropsch liquid delivered into conduit 28 where it may go to storage or to be hydrocracked and then go to stabilization or directly to storage. A light Fischer-Tropsch liquid is delivered into conduit 30, from where it may proceed to storage. A low BTU residual gas or tail gas (substantially $C_5$ or less) is separated from the light FTL product stream and delivered into conduit 22. The residual or tail gas delivered into conduit 22 may be returned to the synthesis gas subsystem 12, where it may be used as a fuel for a combustor of a turbine, or as fuel for burners used within subsystem 12. Synthesis subsystem 16 also produces process condensate stream or byproduct water that is delivered into conduit 32, which delivers the aqueous byproduct to stripper subsystem 14. Synthesis gas subsystem 12 also produces a process condensate stream or byproduct water, which is also carried to stripper subsystem 14 by a conduit, conduit 34. The synthesis subsystem 16, which preferably includes a Fischer-Tropsch reactor, produces aqueous byproducts. If air or enriched air is used as the oxygen-containing gas in the synthesis gas subsystem 16, then the by-product water may include contaminates such as alcohols, most notably ethanol and methanol, and other oxygenates. As noted earlier, the synthesis gas subsystem 12, which preferably includes an autothermal reformer, produces aqueous byproducts that include contaminants such as ammonia and other nitrogen species.

Before the aqueous byproduct streams from subsystems 12 and 16 may be disposed of or utilized elsewhere in the process, the contaminates should be substantially removed or lowered to safe levels, and for this reason, a stripper subsystem 14 is included as an important aspect of the present invention. The treated water from which the contaminates have been substantially removed by stripper subsystem 14 is delivered to conduit 38. From there the treated water may be delivered to other parts of system 10, such as for boiler feed water for use in a closed loop cooling system associated with either a reactor in synthesis gas subsystem 12 or a reactor, such as the Fischer-Tropsch reactor, of synthesis subsystem 16.

Stripper subsystem 14 preferably includes a stripper column and may include a preconditioning unit. A specific embodiment of a stripper subsystem that is preferred is presented below in connection with FIG. 3. For the embodiment shown in FIG. 1, light hydrocarbons such as natural gas, are delivered at ambient conditions to conduit 23, which delivers them to the stripper subsystem 14.

Figure 2:
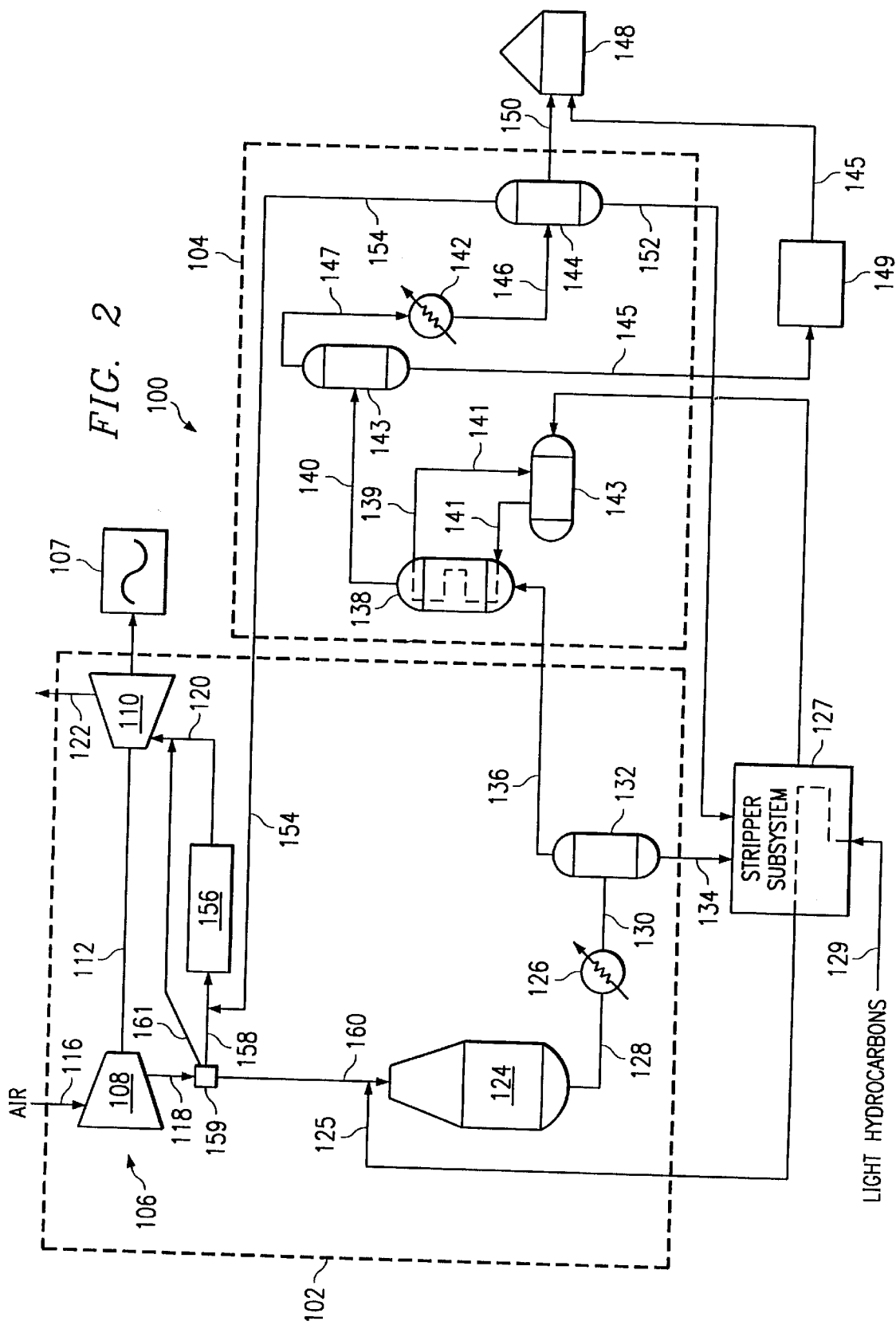
FIG. 2 is a schematic diagram of an embodiment of the present invention.

Referring now to FIG. 2, a system 100 for converting lighter, shorter-chain hydrocarbons to heavier, longer-chain hydrocarbons with an enhanced water disposal subsystem is shown. System 100 is a more specific example of one embodiment that system 10 of FIG. 10 may take. System 100 has a synthesis gas unit, or subsystem 102, that includes a gas turbine 106. System 100 uses gas turbine 106 to provide power for the process at a minimum, but may be designed to provide at least some additional power as shown by electrical generator 107. The power generated by the expansion turbine section 110 drives compressor section 108 by means of linkage 112, which may be, for example, a shaft. Compressor section 108 has an inlet or conduit 116 where compressor 108 receives air. Compressor section 108 also has an outlet or conduit 118 for delivering compressed air for use in preparing synthesis gas. Expansion turbine 110 has an inlet or conduit 120 and an outlet or conduit 122.

Synthesis gas subsystem 102 includes a synthesis gas reactor 124, which is preferably an autothermal reforming reactor (ATR). A stream of gaseous light hydrocarbons, such as a natural gas stream, is delivered to the synthesis gas reactor 124 by inlet or conduit 125. Before such light hydrocarbons are delivered through conduit 125, they are preferably used as a stripping substance in stripper subsystem 127 which may alternatively be thought of as carbon enriching the light hydrocarbons to form an enriched hydrocarbon feedstock. The enriched hydrocarbon feedstock may be formed by stripping carbon containing contaminates from disposed water within stripper subsystem 127. The light hydrocarbons are delivered to a conduit 129, which carries light hydrocarbons to stripper subsystem 127, where the light hydrocarbons may be used to remove contaminates from byproduct water to provide a disposable or treated water stream while simultaneously providing a carbon enriched feedstock, which is delivered to conduit 125. While light hydrocarbons are the preferred gas for stripping contaminates from the byproduct water, tail gas (conduit 154) might also be used; if the tail gas is used, conduit 154 delivers the tail gas to stripper subsystem 127 and then to conduit 158. As another alternative, hot gases from the synthesis gas unit (the effluent in conduit 128) might also be used as the stripping gas. Hydrocarbons in conduit 129 or 125 may also be pretreated to remove sulfur and may be preheated as is known in the art. The light hydrocarbons 129 may alternatively be preheated to improve stripping efficiency. The preheated light hydrocarbon stream will in addition to stripping contaminants, vaporize a portion of the water which can effectivley reduce or eliminate the steam requirements for the synthesis gas system.

Synthesis gas unit or subsystem 102 may also include one or more heat exchangers 126, which in this embodiment is shown as a cooler for reducing the temperature of the synthesis gas exiting outlet 128 of the synthesis gas reactor 124. Heat exchanger 126 delivers its output to inlet 130 of separator 132. Separator 132 removes moisture which is delivered to outlet 134, which in turn delivers the aqueous byproduct to stripper subsystem 127. The synthesis gas exiting through outlet 136 is delivered to synthesis unit or subsystem 104.

Synthesis subsystem 104 may be used to synthesize a number of materials, but is preferably used to synthesize heavier, longer-chain hydrocarbons through a Fischer-Tropsch reaction. Synthesis subsystem 104 includes Fischer-Tropsch reactor 138, which contains an appropriate catalyst, such as a cobalt-based (preferably cobalt supported on alumina) or an iron-based catalyst or other FT Catalyst. Reactor 138 may have a closed loop cooling unit 139 that circulates boiling feed water through conduit 141 from steam drum 143. The output of Fischer-Tropsch reactor 138 is delivered to outlet 140 from where it travels to separator 143. Separator 143 separates the Fischer-Tropsch product into a heavy F-T product that is delivered into conduit 145 and a light F-T product delivered to conduit 147. Conduit 147 delivers the light F-T product to heat exchanger 142 (cooler) and then conduit 146 delivers the cooled product to cold separator 144.

The light F-T product enters separator 144 from conduit 146. Separator 144 distributes the liquid hydrocarbons separated therein to a storage tank or container 148 through conduit 150. Conduit 150 may include additional components such as a conventional fractionation unit. Water withdrawn from separator 144 is delivered to outlet or conduit 152, which delivers the byproduct water or aqueous byproduct stream to stripper subsystem 127.

The heavy F-T product delivered by separator 143 into conduit 145 which delivers it to product storage, e.g., storage 148. A hydrocracker, e.g., hydrocracker 149, or other downstream processing systems and devices may be included on conduit 145. The F-T products of conduits 150 and 145 may be or be used to make numerous products as mentioned elsewhere herein.

System 100 includes, as an aspect of synthesis gas subsystem 102, a combustor 156. Combustor 156 receives air from compression section 108, delivered through conduit 158, from a control unit 159. Control unit 159 may be used to control compressed air from conduit 118 as between its delivery to conduit 158 and on to combustor 156, (or in some instances through conduit 161 to conduit 120 and on to expansion section 110), or into conduit 160 and on to synthesis gas reactor 124. Control unit 159 may be used to help control the temperature in combustor 156 and in expansion section 110. Conduits 118, 158, and 161 are shown as they are for illustrative purposes. It should be understood that for most gas turbines, these conduits are integral to the gas turbine compressor case. The control unit 159 is typically a combination of internal flow orifices within the combustor 156 and external control units located in conduit 160 to control the flow of air to the synthesis gas reactor 124.

A low-BTU residue gas or tail gas, which may have a heating value less than 100 BTU/scf, is delivered by separator 144 into conduit 154 is fluidly coupled to combustor 156. Tail gas within conduit 154 is delivered directly to combustor 156 or to conduit 158 and then to combustor 156. To maintain the desired flows, it may be necessary in some instances to add a booster compressor on conduit 154 to increase the pressure of the tail gas to slightly greater than the compressed air delivered into conduit 158 or alternatively to locate a device in conduit 158 to drop the pressure of the compressed air sufficiently to allow the tail pressure to be slightly greater.

Control unit 159 may also drop the pressure. The output of combustor 156 is delivered to expansion turbine 110.

Combustor 156 may include a catalyst that is useful for promoting combustion reactions. The combustion-promoting catalyst may facilitate combustion of low BTU gases in combustor 156. Oxidizing catalyst known in the art may be used such as an active metal from the platinum group, cobalt, lanthanum, palladium, rhodium, nickel, iron, copper, manganese, chromium, molybdenum, titanium, silver, cerium, and the like. The added catalyst may be in the form of a ceramic honeycomb insert with the oxidizing catalyst impregnated thereon.

The preferred operating pressure in the synthesis gas subsystem 102 described in connection with FIG. 2 is in the range of 50 psig to 500 psig, and more preferably, in the range of 100 psig to 400 psig. The relatively low operating pressure has the benefit of being in the range of most gas turbines, so additional compression is minimized. Also, the operating of the synthesis gas production unit 102 at relatively low pressure has the benefit of improved efficiency of the reforming reactions resulting in higher conversion of carbonaceous feeds like natural gas into carbon monoxide instead of carbon dioxide. Additionally, undesirable reactions that lead to the formation of carbon are less likely to occur at low pressures. The temperature of reactor 124 may be in the range of 1600–2200 degrees Fahrenheit. The Fischer-Tropsch reactor 138 preferably operates in the range of 0 to 500 epsia and at a temperature of 250 to 550 degrees Fahrenheit. If the lower pressure reactor 124 is used, it may be necessary to add a booster compressor between subsystem 102 and subsystem 104.

Figure 3:
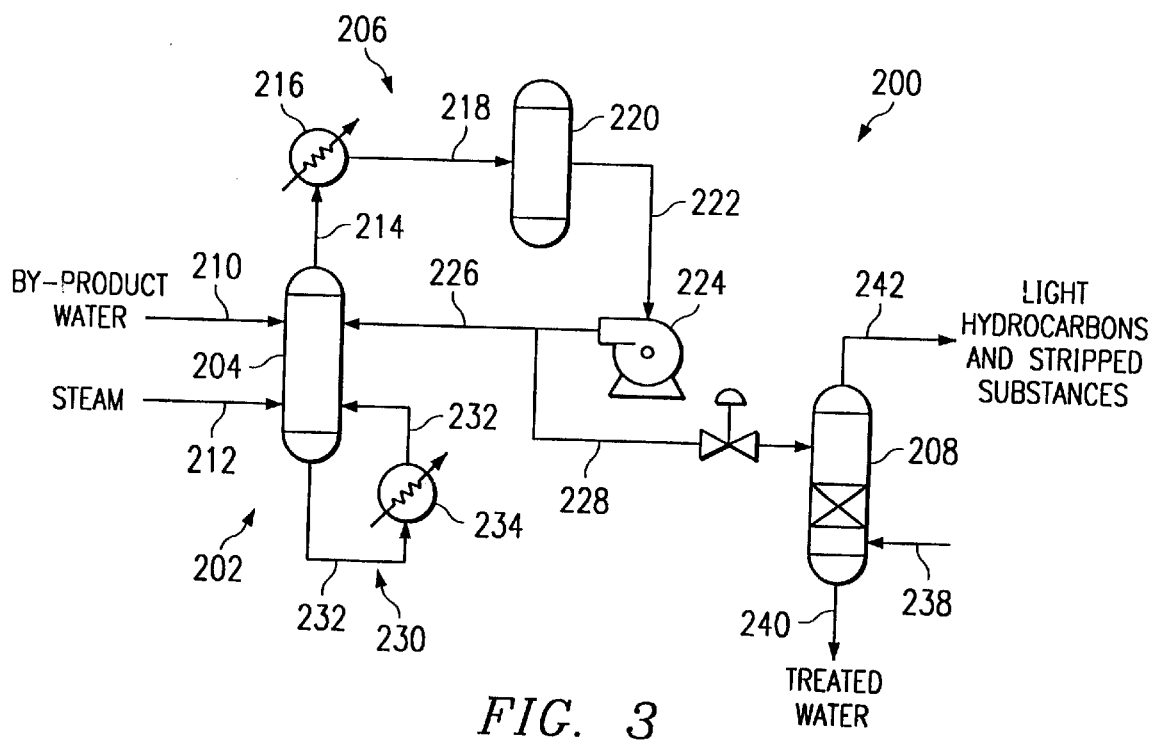
FIG. 3 is a schematic diagram of one embodiment of a stripper subsystem according to an aspect of the present invention.

Referring now to FIG. 3, one embodiment of a stripper subsystem 200 is shown. As an important aspect of the present invention, stripper subsystem 200 may include a preconditioning unit 202 that includes a concentrator column 204 with a reflux unit 206. The preconditioning unit 202 is used primarily to adjust the vapor-to-liquid (V-L) ratio. The Fischer-Tropsch process produces more water than liquid products. In air-based systems, alcohols are also produced—many of which are water-soluble. The lighter alcohols, primarily methanol and ethanol, are very sensitive to water and will remain in the aqueous phase during the process when the aqueous phase is separated from the liquid hydrocarbon phase. The resulting alcohol and water solution (aqueous phase), however, has a relatively low alcohol concentration, typically less than 3-wt. % alcohol. A large vapor rate (high V/L ratio) is desirable to strip the small quantity of alcohol from a large quantity of water and produce a relativley pure water effluent. High vapor temperature and/or lower stripping pressure improve stripping efficiency. An important aspect of the present invention includes concentrating the alcohol contaminates in the byproduct water stream prior to the time that they are stripped in a stripper column 208. The alcohol content may be concentrated by heating the water and driving the alcohols and a portion of the water over head.

The aqueous byproducts or byproduct water stream is delivered through conduit 210 to concentrator column 204. Steam is delivered through conduit 212 to concentrator column 204. As noted before, the heating of the water drives the alcohols and a small portion of the water over head into conduit 214. The products in conduit 214 are condensed with heat exchanger 216 and delivered to conduit 218 to a reflux drum 220. The accumulated product in reflux drum 220 is delivered into conduit 222 to pump 224 from where a portion is used as a reflux for the concentrator column 204 and is delivered through conduit 226 (for rectification purposes) and another portion to conduit 228 for delivery to stripper column 208. Heat may be added to concentrator column 204 by steam injection shown with conduit 212, or indirectly with heating loop 230, or both. Heating loop 230 has a series of conduits 232 with a heating unit 234, such as a heat exchanger therein.

The net product from preconditioning unit 202 is delivered through conduit 228 to stripper column 208. Stripper column 208 may have a lower stripping section and an upper rectification section. Stripper column 208 preferably contains a high efficiency packing to minimize the height of the column and is made of a simple carbon steel pressure vessel with a mass transfer media used as a packing that enhances the surface area so that the stripping gas or substance separates the alcohol from the water efficiently. Stripper Column 208 preferably has some type of separation media that provides surface area for the stripper substance or gas to preferentially drive the alcohol over head and allow the water to flow to the bottom of the column. The stripper substance, which is preferably natural gas feedstock (e.g., 129 in FIG. 2), is delivered through conduit 238 to stripper column 208. In other embodiments of stripper subsystem 200, the stripping substance may be air. The natural gas delivered in conduit 238 is preferably at a pressure in the range of 0–200 psig and a temperature of 50–200 degrees Fahrenheit. The stripper substance is introduced at the bottom of column 208 below the packing, and the contaminated water is introduced at the top through conduit 228. As the stripping substance and water pass counter-currently, the alcohol contaminates go preferentially with the stripper substance because of its volatility and the water is essentially cleaned from column to column.

The treated water exits column 208 through conduit 240. The treated water in conduit 240 may be disposed of and is preferably delivered for use within a system for converting the lighter hydrocarbons to longer-chain hydrocarbons and more preferably still to be used as boiler feed water make-up or cooling tower make-up in either the Fischer-Tropsch reactor or the synthesis gas reactor. The treated water delivered to conduit 240 may be stripped such that contaminates therein are in parts per million. The contaminates which have been stripped, which are largely carbon containing contaminates, are removed along with the stripping substance through conduit 242 and form a carbon-enhanced feedstock that may be delivered to a synthesis gas subsystem (such as subsystem 12 of FIG. 1).

Figure 4:
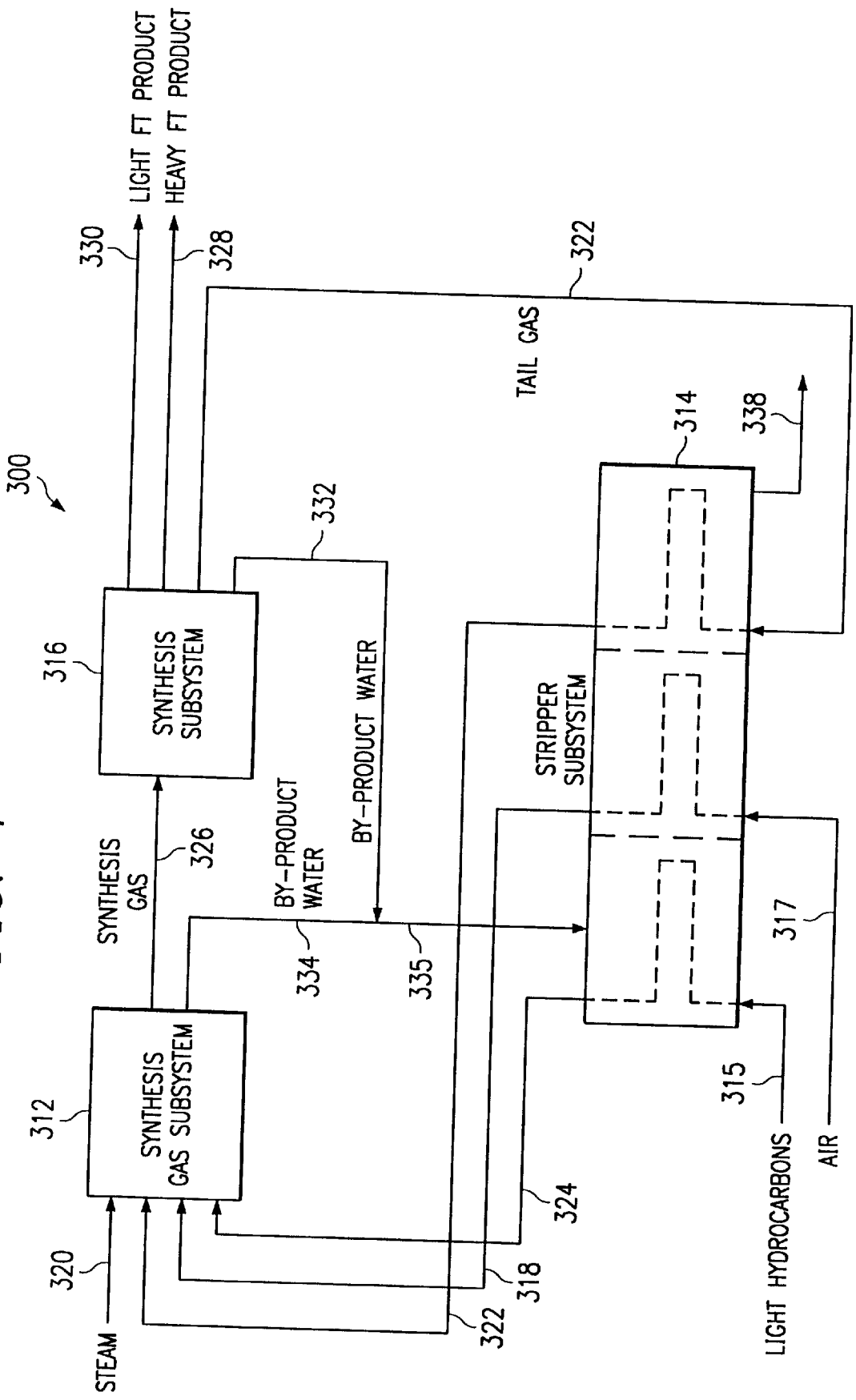
FIG. 4 is a schematic diagram of another embodiment of the present invention.

Referring now to FIG. 4, another embodiment of a system 300 for converting lighter, shorter-chain hydrocarbons to heavier, longer-chain hydrocarbons with enhanced water disposal is presented. System 300 is in most respects analogous to that presented in FIG. 1, except three of the plurality of feedstocks to synthesis gas subsystem 312 are used by stripper subsystem 314. While three are shown used, it is to be understood that only two could alternatively be used. The stripper subsystem 314 is shown with the feedstocks being used in series, but a parallel use of the feed streams might be used as well.

Synthesis gas subsystem 312 receives steam through conduit 320; tail gas through conduit 322, which has been carbon enhanced by its use in stripper subsystem 314; air delivered through conduit 318, which has also been carbon enhanced by its use in stripper subsystem 314; and a light hydrocarbon feedstock delivered through conduit 324, which has also been carbon enhanced by its use in stripper subsystem 314. Synthesis gas subsystem 312 produces a synthesis gas and delivers it through conduit 326 to synthesis subsystem 316. Synthesis gas subsystem 316 synthesizes the synthesis gas to form a light Fischer-Tropsch product that is delivered to conduit 330 and a heavy Fischer-Tropsch product that is delivered to conduit 328. A residue gas or tail gas (substantially $C_5$ and less) is delivered to conduit 322. Synthesis subsystem 316 produces a byproduct water delivered to conduit 332. A byproduct water is also produced by synthesis gas subsystem 312 and delivered to conduit 334. The byproduct water streams from the subsystems 312 and 316 are delivered through conduit 335 to stripper subsystem 314.

Stripper subsystem 314 for the embodiment shown receives light hydrocarbons through conduit 315; air through conduit 317; and a tail gas through conduit 322. Stripper subsystem 314 may use a preconditioning unit like unit 202 of FIG. 3 and a multi-section or plurality of stripper columns, each like stripper column 208 of FIG. 3. The byproduct water of conduit 335 is stripped or cleaned to the desired level by stripper subsystem 314 and delivered to conduit 338, where it may be disposed of preferably by use within system 300 for such things as cooling of a Fischer-Tropsch reactor within synthesis subsystem 316.

Figure 5:
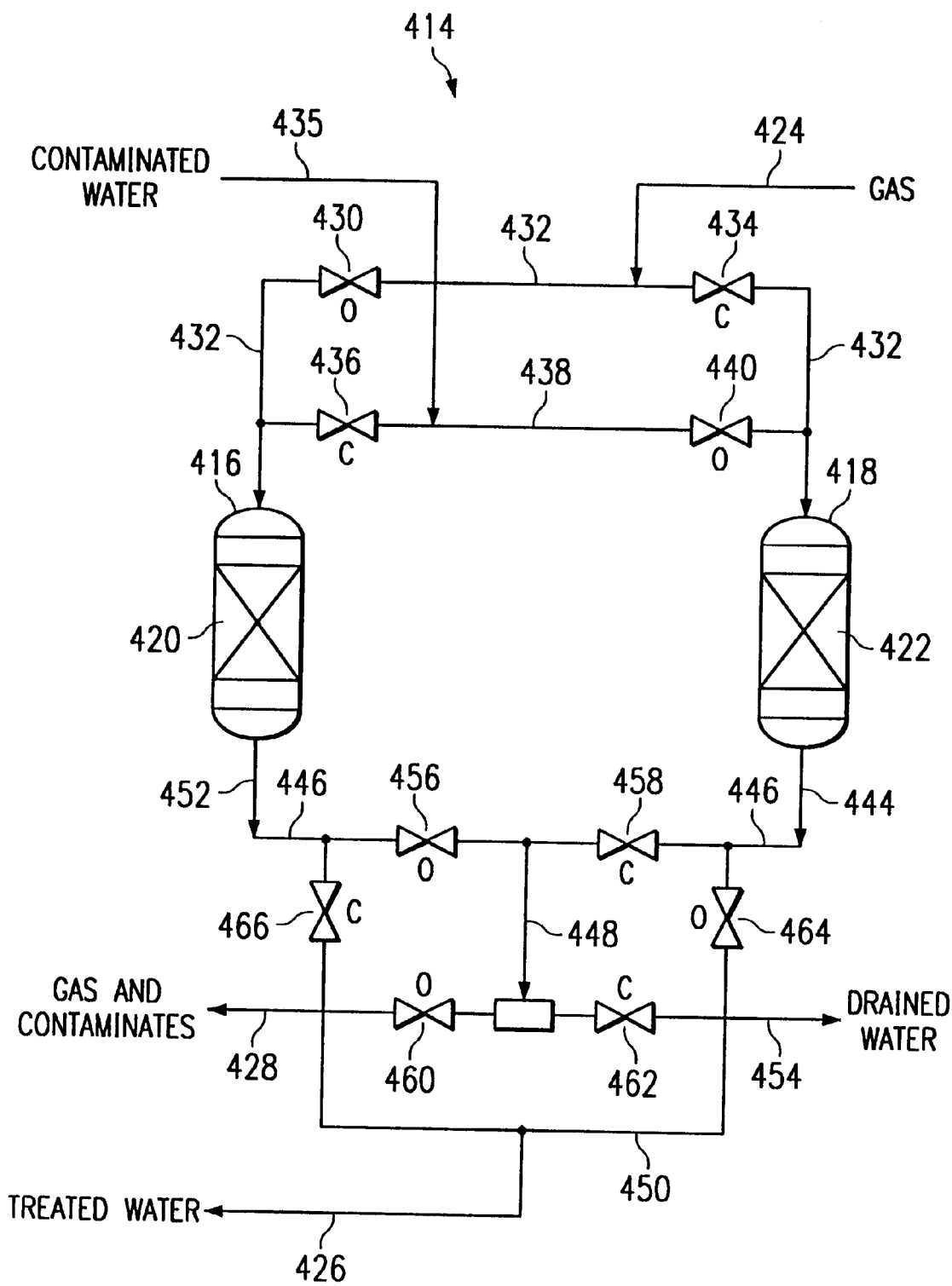
FIG. 5 is a schematic diagram of a contaminate removal subystem using activated carbon.

Referring now to FIG. 5, another embodiment of a stripper (contaminate removal) subsystem 414 is presented. Subsystem 414 uses activated carbon to remove contaminates from the by-product water that is introduced to the subsystem through conduit 435. Preferably at least two vessels 416 and 418 hold the activated carbon beds 420 and 422, respectively. Having at least two vessels facilitates alternating batch processing as explained further below. The activated carbon is used to adsorb contaminates in by-product water passing through the vessel. Once the carbon in the vessel is sufficiently saturated, it may be taken off line and regenerated with a hot gas or air introduced to the subsystem 414 through conduit 424. The treated water is removed from the subsystem 414 through conduit 426 and the gas (or air) with contaminates from the regeneration process are removed from the subsystem through conduit 428.

In one mode of operation, valve 430 on conduit 432 is open; valve 434 is closed; valve 436 on conduit 438 is closed, and valve 440 is open. Thus, contaminated water delivered through conduit 435 is delivered to vessel 418, and meanwhile the carbon bed in vessel 416 may be regenerated with hot air delivered to it through conduit 424. The purified water that is substantially free of contaminates is delivered into conduit 444 which is fluidly coupled to conduits 446, 450, and 426, with valves 458 and 466 closed and valve 464 open, whereby the treated water exits subsystem 414. It is to be appreciated that by changing the status of the valves, vessel 416 may be used in a like manner to remove contaminates from the water.

When vessel 418 is in use as described above, the carbon bed of vessel 416 may be regenerated. To do this, the water in the bed may first be drained with the drained water going through conduits 452, 446, 448, and out conduit 454 (valve 456 is open; valve 458 is closed; valve 460 is closed; and valve 462 is open). Once drained, hot air is delivered through conduit 424 to conduit 432 to vessel 416. The hot air passes through the carbon bed removing contaminates and regenerating the bed. Then the hot air exits through conduit 452 and passes through conduit 446 (valve 456 is open) to conduit 448. With valve 462 closed and valve 460 open, the hot gas and contaminates exit subsystem 414 through conduit 428 from where they may be delivered to a synthesis gas subsystem to be used therein.

The Fischer-Tropsch systems and processes described herein may be used to make numerous longer-chain hydrocarbons, e.g., the full spectrum of $C_{5+}$ products through the Fischer-Tropsch reaction (but other reactions might be used in some situations) and may be adapted to accommodate numerous environments and applications. The longer-chain Fischer-Tropsch products that may be made directly or With some downstream processing include numerous products for numerous uses. A number of examples are presented below.

The Fischer-Tropsch products may include synthetic alpha olefins adapted for many applications, including, without limitation, PAO feedstock (alpha olefins in the range of $C_6$ to $C_{12}$ and preferably $C_{10}$ are used to produce poly alpha olefins); alpha olefins for laundry and other detergents (preferably $C_{12}$–$C_{16}$); chlorination stock to be used in textiles, pharmaceuticals and transportation lubricants/hydraulic fluids (preferably $C_{18}$–$C_{24}$); alpha olefins used to produce particle board emulsions and poly vinyl chloride lubricants ($C_{24}$–$C_{28}$); and alpha olefins used to manufacture decorative and industrial candles, particle board emulsions and PVC lubricants ($C_{30}$ + alpha olefins, which are considered a synthetic paraffin wax and therefore used in many of the markets where paraffin waxes are used). The Fischer-Tropsch products are also well suited for use as a synthetic white oils because Fischer-Tropsch liquid normal paraffins meet FDA specifications governing their use in direct food contact applications, which gives them a wide range of potential markets to enter, including markets which traditionally use food grade mineral oils. Similarly, the Fischer-Tropsch product may be used for technical grade mineral or white oils that are used to produce paints, stains and inks, among other end-use products and may be used as a pharmaceutical (USP) grade white oil to be used to produce cosmetics and healthcare products. In these applications, Fischer-Tropsch products are better because the liquid or hydroisomerized product can probably satisfy ASTM standards with little effort.

The Fischer-Tropsch products may also be used for synthetic liquid n-paraffins in numerous applications. The Fischer-Tropsch product may be used as a chlorination feedstock to be used, for example, to produce chlorinated normal paraffins for use in textiles and industrial lubricants. The product may also be used as a linear alkyl benzene (LAB) feedstock ($C_{10}$ to $C_{13}$) which may be used for laundry detergents. The Fischer-Tropsch product may also be used as an aluminum rolling oil ($C_{14}$ to $C_{17}$), e.g., for cold rolling oils for aluminum foil. Further the Fischer-Tropsch product N-paraffin may be used for "liquid" candles.

The Fischer-Tropsch product may be used as a synthetic wax in numerous applications. For example, the product may be used to make thermostat wax, which is used primarily to control automobile thermostats. The wax is particularly suitable for this since it must be uniform in molecular weight, carbon number distribution and molecular structure. The Fischer-Tropsch wax may be used to make hotmelt adhesives, i.e., used as a viscosity modifier for industrial hotmelt adhesives. The synthetic wax may be used in printing inks. In that case, the wax is used as an antiscuff surface modifier for fine grade web offset and gravure inks. It may also be used for paints and stains. The wax is used to enhance water repellency of water-based paints and stains. The Fischer-Tropsch product may be used to make corrugated board in which the waxes are used to add strength and water repellency to the corrugated board. Similarly, the Fischer-Tropsch product may also be used as a wax for packaging and food additives.

The synthetic wax may be used as a PVC lubricant/extrusion aid; the high melting point waxes are used as internal/external lubricants for PVC extrusion. The wax may be used as a flushing compound, to impart the dripless quality to decorative candles, with cosmetics as a viscosity modifier and melting point enhancer, to bind various drugs which are in powdered form into tablet form (they also impart a slippery surface to tablets such as aspirin, etc.). Waxy Fischer-Tropsch products may also be used as plasticizers and extrusion aids for various plastics such as high density polyethylene, PET linear low density polyethylene and polypropylene. Another use is as anti-ozone additives to protect the outside surfaces of rubber products from packing and ozone damages.

Fischer-Tropsch product in the form of synthetic lubricants may be used in numerous additional applications. For example, the synthetic lubricants may be used as environmentally friendly drilling fluids. Fischer-Tropsch oils may be used to produce highly stable high temperature operation automatic transmission fluids. They may also be used as a hydraulic fluid that is very stable at high temperatures and ideally suited for use in vehicular and industrial hydraulic compounds. The synthetic lubricants may also be used as vehicular lubricants (PCMO and HDD). The Fischer-Tropsch product in the form of a synthetic lubricant may be used as a quenching oil or cutting oil. Further they may be used for a plurality of specialty lubricants such as for two-cycle, marine lubricants, or baroil. They may also be used as a vehicle for lubricant-additives.

An exciting aspect of the products that may be made from or as part of the Fischer-Tropsch products are synthetic fuels and blends, including Fischer-Tropsch compression ignition fuels, Fischer-Tropsch spark ignition fuels, feedstocks for fuel cells, aviation fuel (turbine and spark-ignition) and railroad fuels. The sulfur-free clean nature of the synthetic fuels thus made are advantageous.

The Fischer-Tropsch products may also be used as synthetic solvents. As such, the uses of the synthetic solvents include as printing inks, paints, stains, drying agents, dye transfer agents, synthetic heptane, hexane, and de-waxing agents.

The process, such as that presented in connection with FIG. 2, may be adapted with other plants for additional purposes and may also be modified for application in the various environments throughout the world. Fischer-Tropsch plants can be built in a number of different settings, which will, by definition, determine some of the plant characteristics. The following is a list of some of the settings in which Fischer-Tropsch plants may be applied. The character of these plants will be controlled by factors including weather conditions, specifically whether it is tropical or temperate, or arctic settings, as well as local conditions, such as wind, wave action, altitude and precipitation.

Land-based plants imply the absence of water, and can have permanent or temporary foundations. Sites will range from sea level to elevations limited by turbine capability. Further adjustments are made for certain plant conditions such as arctic weather conditions on the North Slope. Riverine/Deltaic Fischer-Tropsch plants generally are capable of accommodating fluctuating water levels due to flood conditions, consolidated soil, regional subsidence, and other dynamic conditions common to this setting. Intratidal Fischer-Tropsch plants include many of the same conditions as Riverine/Deltaic Fischer-Tropsch plants, but also include design consideration known in the art for tides and wave motion. Open water Fischer-Tropsch plants are engineered to accommodate wind and waves motions found in open marine conditions.

Numerous platform options are available for Fischer-Tropsch plants to help accommodate their application in the various settings and conditions. The following listing is a brief characterization of bases or platforms on Fischer-Tropsch plants may be mounted. A barge-mounted Fischer-Tropsch plant may be used in marine, intratidal, and Deltaic/Riverine settings. The Fischer-Tropsch plants may be made from material ranging from metal to concrete. A plant may be mounted on a ship or FSPO primarily for an open marine condition(s), and may be utilized under conditions similar to FSPO (oil production) today. The plants may be modular (e.g., steel skid-mounted containers). These modular Fischer-Tropsch plants are subdivided into modules on steel skid-mounted containers for efficient transport, setup, connect and disconnect. Modular Fischer-Tropsch plants may range in sizes from small enough for shipment by rail to large enough to be carried as a heavy lift from a barge or ship. The plants may also be spar/offshore platform mounted Fischer-Tropsch plants. These Fischer-Tropsch plants are mounted on offshore and open marine settings spar or platforms, either retrofitted onto platforms that were previously designed for offshore oil and gas production or on platforms built specifically for the Fischer-Tropsch plant. The Fischer-Tropsch plant on a vessel may also be modified for use in recovering and converting hydrates from the ocean floor. These are but a few examples. In addition to these platforms and settings, the plants may be oriented toward numerous other or additional applications. For example, the plant may be an aspect of a desalination plant. These Fischer-Tropsch plants are designed to use Fischer-Tropsch process heat (the Fischer-Tropsch and syngas reactions) to convert available water into water suitable for agriculture, industrial or portable water. The desalination may be by reverse osmosis or thermal desalination.

Although the present invention and its advantages have been described in detail, it should be understood that various changes, substitutions, and alterations can be made therein without departing from the spirit and scope of the invention as defined by the following claims.

What is claimed is:

1. A method for producing heavier hydrocarbons from lighter hydrocarbons, the method comprising the steps of:

reacting an oxygen-containing gas and a light hydrocarbon feedstock to produce a synthesis gas;

delivering the synthesis gas to a Fischer-Tropsch reactor;

converting the synthesis gas into an effluent containing heavier hydrocarbons;

separating an aqueous byproduct stream from the effluent;

removing contaminates from the aqueous byproduct stream; and wherein the step of removing contaminates from the aqueous byproduct stream comprises the steps of:

concentrating the contaminates in a concentrator column to produce a concentrated contaminate effluent, condensing the concentrated contaminate effluent to form a concentrated condensate stream, accumulating the concentrated condensate stream in a reflux drum, and using a stripping gas in a stripper column to remove the contaminates from at least a portion of the concentrated condensate stream to produce a treated water stream and a stream containing contaminates and the stripping gas.

2. The method of claim 1 wherein the step of using a stripping gas comprises the step of using a light hydrocarbon stream to strip the contaminates.

3. The method of claim 1 wherein the step of converting the synthesis gas into an effluent containing heavier hydrocarbons further comprises preparing a tail gas and wherein the step of using a stripping gas comprises the step of using the tail gas as the stripping gas.

4. A method for producing longer-chain hydrocarbons from shorter-chain hydrocarbons, the method comprising the steps of:

using a plurality of feedstocks that comprise air and light hydrocarbons in a synthesis gas unit to produce a synthesis gas;

delivering the synthesis gas to a Fischer-Tropsch reactor;

using a Fischer-Tropsch reaction in the Fischer-Tropsch reactor to convert the synthesis gas into heavier hydrocarbons; and removing contaminates from an aqueous byproduct stream by concentrating the contaminates and using at least one of the plurality of feedstocks in a stripper column to produce a treated water stream.

5. The method of claim 4 further comprising the step of introducing the removed contaminates into the light hydrocarbon feedstock before the feedstock is delivered to the synthesis gas unit.

6. The method of claim 4 wherein air and light hydrocarbons are used in a stripper in series.

7. The method of claim 4 further comprising the step of using the treated water stream for cooling in the Fischer-Tropsch reactor.

8. A method for producing heavier hydrocarbons from light hydrocarbons, the method comprising the steps of:

using a plurality of feed stocks, which comprise air and light hydrocarbons, in a synthesis gas unit to produce a synthesis gas;

delivering the synthesis gas to a Fischer-Tropsch reactor to convert the synthesis gas into a product stream containing heavier hydrocarbons;

separating an aqueous byproduct stream from the product stream;

concentrating the contaminates in the aqueous byproduct stream with a concentrator column to form a concentrated contaminate stream; and removing contaminates from the concentrated contaminate stream with a vessel containing activated carbon.

* * * * *